United States Patent [19]

Iskra

[11] Patent Number: 4,596,567

[45] Date of Patent: Jun. 24, 1986

[54] PERF-EMBOSSED ABSORBENT STRUCTURE

[75] Inventor: Michael J. Iskra, Flemington, N.J.

[73] Assignee: Personal Products Company, Milltown, N.J.

[21] Appl. No.: 641,548

[22] Filed: Aug. 17, 1984

[51] Int. Cl.⁴ .............................................. A61F 13/16
[52] U.S. Cl. .................................................... 604/368
[58] Field of Search .............. 604/368, 379, 378, 380, 604/381, 382, 383, 374, 375, 367, 385

[56] References Cited

U.S. PATENT DOCUMENTS

| Re. 26,151 | 1/1967 | Duncan et al. | 604/379 |
| 2,788,003 | 4/1957 | Morin | 604/379 |
| 4,102,340 | 7/1978 | Mesek et al. | 604/379 |
| 4,186,165 | 1/1980 | Aberson et al. | 604/379 |
| 4,340,057 | 7/1982 | Bloch et al. | 604/379 |
| 4,500,315 | 2/1985 | Pieniak et al. | 604/379 |

Primary Examiner—John D. Yasko
Attorney, Agent, or Firm—Martha A. Michaels

[57] ABSTRACT

A soft, perf-embossed, absorbent composite structure is provided which comprises an absorbing layer of a fibrous web containing at least about 200 percent by weight of superabsorbent and a wicking layer. The composite structure has a Taber stiffness value less than about 30.

9 Claims, 7 Drawing Figures

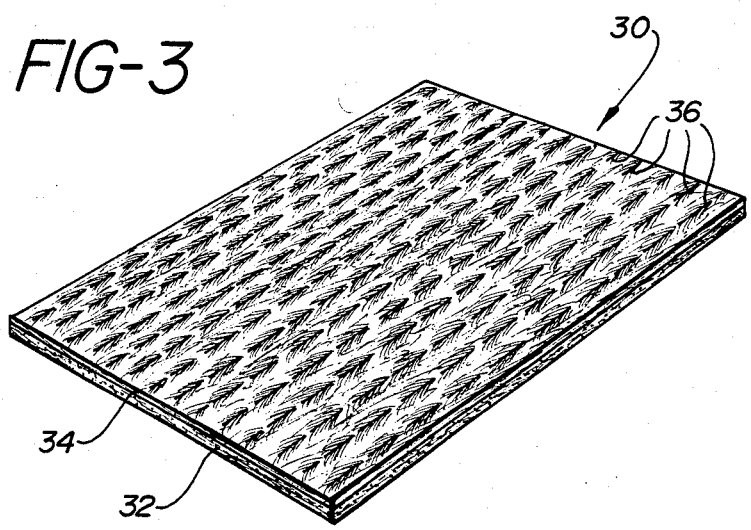
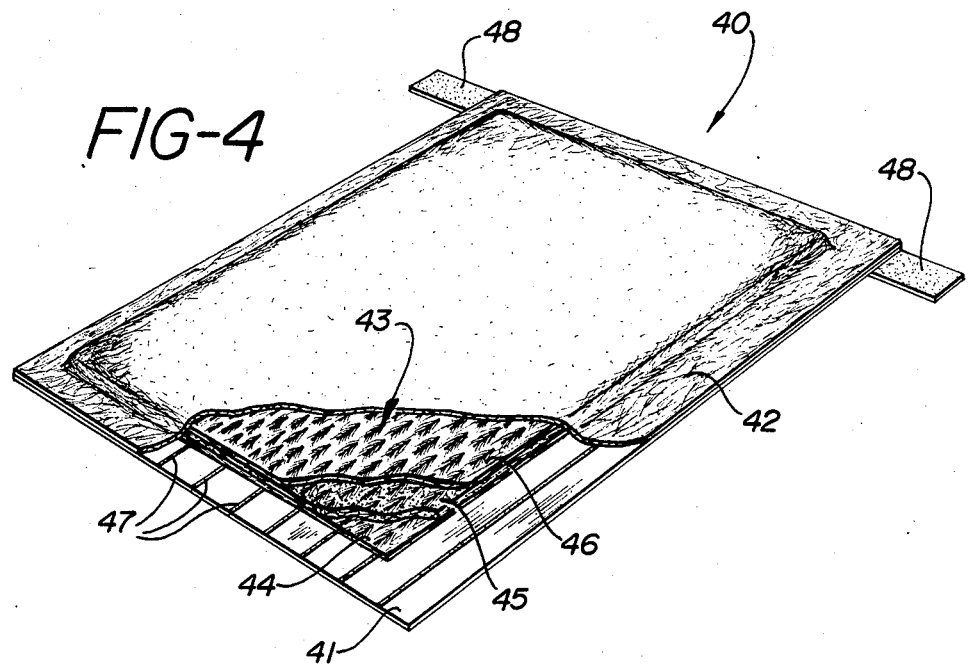

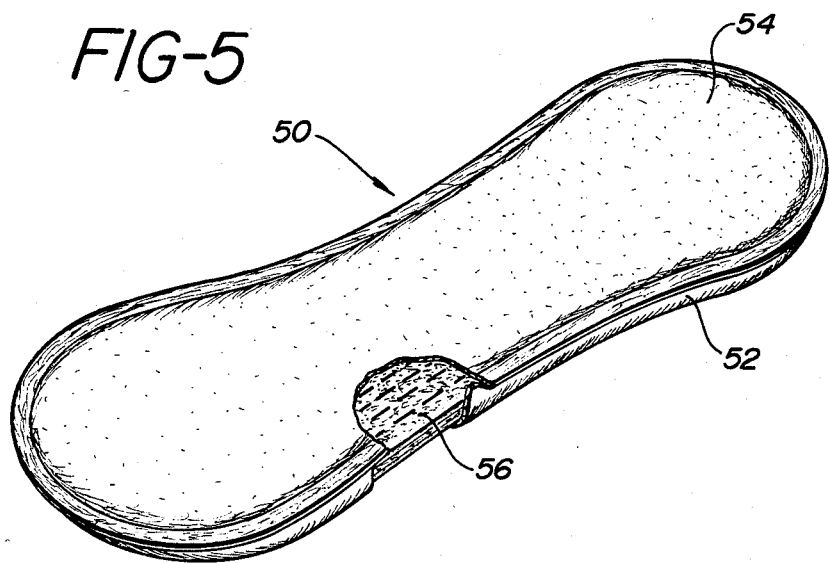

PERF-EMBOSSED ABSORBENT STRUCTURE

BACKGROUND OF THE INVENTION

The present invention relates to a new and improved thin absorbent structure, and more particularly, to a new and improved compressed absorbent composite containing superabsorbent material, and which composite absorbs large quantities of liquids.

Disposable absorbent products have been known for some time including such products as disposable diapers, sanitary napkins, wound dressings, bandages, incontinent pads, and the like. These products incorporate an absorbent batt which is used to absorb and hold, or contain, body fluids. Initially, in many of these products, especially diapers and sanitary napkins, the absorbent batt consisted of what is termed "wadding" or plies of tissue. The wadding was disposed between an impermeable backing and a permeable facing and the plies of tissue were used to absorb and hopefully contain the liquid within the product. A diaper which utilizes such an absorbent batt is disclosed in U.S. Pat. No. Re. 26,151.

The wadding type of batt was replaced for the most part by an improved absorbent batt which comprises what is termed "fluffed wood pulp fibers". This absorbent batt comprises a layer of individualized wood pulp fibers with the layer having substantial thickness. A diaper which incorporates such a fluffed wood pulp absorbent batt is described in U.S. Pat. No. 2,788,003. This diaper had improved absorbent capacity and somewhat better containment than a diaper using a wadding layer. Also, the fluffed wood pulp layer is quite soft, flexible, and conformable, and hence produces an improved diaper over diapers using wadding as the absorbent layer.

Though the fluffed wood pulp absorbent batts have improved capacity, the efficiency with which the capacity is used in a diaper or sanitary napkin is poor. The reason for this is that the fluid to be absorbed is generally deposited in a localized area within the absorbent batt and the ability for the fluid to move along the plane of the batt is poor. The fluid follows the path of least resistance, and consequently moves to the closest edge of the batt where it generally is no longer contained and the product leaks. Furthermore, the wood pulp batts lack stability, e.g., when a diaper is being worn, the batt tends to break up creating bunching.

U.S. Pat. No. 3,017,304 discloses an absorbent product which incorporates a fluffed wood pulp absorbent batt having a densified paper-like layer. This paper-like layer acts as a wick, i.e., liquid which is placed on the layer tends to move rapidly along the plane of the layer. When incorporated in combination with fluffed wood pulp fibers, the resultant product uses the absorbent capacity of the fluffed wood pulp much more efficiently. Diapers which incorporate this paper-like layer combined with fluffed wood pulp are disclosed and described in U.S. Pat. Nos. 3,612,055 and 3,938,522. This concept of combining a wicking layer or capillary skin with fluffed wood pulp fibers has gained wide acceptance in many absorbent products including disposable diapers and sanitary napkins. Even though these products make much greater use of the capacity of the absorbent batt, they still do not totally contain the absorbed liquid. It is probable that these products will leak before the full capacity of the batt is used for absorption. This is especially true if pressure is placed on the batt while wet. For example, a baby sitting down on a previously wetted diaper will very often cause the batt to leak. Although the batt is somewhat stabilized by the paper-like densified skin, it may crack and separate.

A number of years ago "superabsorbent materials", i.e., materials which will absorb many times their weight of liquid, were developed. Since the development of such materials, people have been trying to incorporate them in absorbent products such as diapers and sanitary napkins to enhance the absorptive performance of these products. Theoretically, a minimum amount of superabsorbent incorporated in a product would make that product perform as well or better than the prior art products. Perhaps one of the first products to incorporate such a superabsorbent material in a disposable diaper is disclosed in U.S. Pat. No. 3,670,731. This patent discloses an absorbent dressing comprising an absorbent layer sandwiched between a permeable facing and an impermeable backing sheet. The absorbent layer contains water insoluble, crosslinked, hydrocolloid polymer as the absorbent material.

Even though absorbent materials have been available for some time, they have not gained wide acceptance in absorbent products such as disposable diapers and sanitary napkins. A primary reason for this lack of acceptance of the superabsorbents is failure to develop a product capable of economically utilizing the highly increased absorptive capacity of the superabsorbent material. In order to economically utilize the superabsorbent, the liquid being absorbed must be transported to the superabsorbent material. In other words, the superabsorbent material must be placed in contact with the liquid.

Furthermore, as the superabsorbent material absorbs the liquid, it must be allowed to swell. If the superabsorbent is prevented from swelling, it will cease absorbing liquid. Hence, if the superabsorbent material is to function in diapers and sanitary napkins wherein the liquid to be absorbed is placed in a small void area, the structure of the absorbing layer containing superabsorbent material appears to be critical. Over the years, a number of techniques have been disclosed in an attempt to provide structures which make efficient use of the superabsorbent material, such products are disclosed in U.S. Pat. Nos. 4,103,062; 4,102,340; and 4,235,237. In addition, methods for incorporating superabsorbents into suitable layers or suitable configurations which can be placed in an absorbent product are disclosed in U.S. Pat. Nos. 4,186,165; 4,340,057; and 4,364,992. To date, none of these products has met with any substantial commercial success.

In an attempt to overcome these problems, in copending application Ser. No. 439,963 filed Nov. 8, 1982, a particularly useful compressed composite structure is formed. Application Ser. No. 439,963 is hereby incorporated by reference. The compressed composite is a layered structure which contains an absorbing layer, a wicking layer and a transition zone. The product is compressed. The absorbing layer is generally a high loft, nonwoven, fabric such as polyester, which layer contains at least 200 percent superabsorbent. Although this layer potentially has high liquid-absorption capability, it is necessary to provide a transporting mechanism so that liquid which is deposited locally on the superabsorbentcontaining web can be transported. In order to provide this, a wicking layer is placed on the absorbing layer and the two layers are compressed, thus providing a transition zone at the contact point of the two layers. The wicking layer generally is a wood pulp fiber layer. Although the resulting compressed composite readily accepts, transports, and absorbs liquid, the product is somewhat stiff, and hence requires softening to provide flexibility for utilization in products such as diapers and the like. The flexibility provided needs to be permanent, i.e., the surrounding environment, handling of the product, and its subsequent use will not affect the softness and flexibility.

The present invention provides a new and improved absorbent composite structure which utilizes a substantial portion of the absorptive capacity of superabsorbent materials and yet is reasonably soft and flexible. This composite remains in its substantially, completely, stable state, though rendered soft and flexible. Whether wet or dry the composite does not break, bunch, or separate. Furthermore, the composite retains absorbed liquid without yielding any of the liquid when the composite is under pressure.

SUMMARY OF THE INVENTION

The present invention provides an absorbent composite structure which is comprised of an absorbing layer and a wicking layer, the absorbing layer containing at least about 200 percent by weight superabsorbent. The absorbent composite is perf-embossed to reduce its Taber stiffness value by at least 75 percent to a Taber stiffness value of about 30 or less.

The perf-embossing is carried out by known techniques such as that exemplified in U.S. Pat. No. 3,817,827. In order for the absorbent composite to be softened and reduced substantially in Taber stiffness, it is necessary to attain the glass transition temperature of the superabsorbent material so that the superabsorbent polymer is brittle and can be reduced in size effectively by the mechanical working and crushing provided by the perf embossing. The glass transition temperature is reached by reducing the moisture content sufficiently to permit satisfactory operation at the temperature of the room in which the operation is being carried out. For most superabsorbent materials, the satisfactory moisture content is less than about 10 percent by weight of moisture of the composite structure.

The perf-embossing should provide sufficient impact points on the product to reduce the superabsorbent polymer particle size. Generally, if the impact points are no more than ¼ inch apart and are somewhat continuous, a satisfactory change in Taber stiffness value will be achieved. In the process of perf-embossing, the composite is passed through a pair of rolls which have knuckles and which intermesh to shear the composite in the desired fashion. When looking at the composite after it has been perf-embossed, there are raised areas produced by lower knuckles and adjacent depressions produced by upper knuckles. If the composite is viewed from the other side, the raised areas become depressions and the depressions become raised areas. The depressions are densified regions which hold and wick liquid. Interconnecting the raised areas and the depressions are intermediate portions which have received most of the mechanical working which reduces the superabsorbent polymer size and fuses the layers of the composite together in the shear areas. At locations where the upper knuckles pass very close to the lower knuckles of the embossing rolls, the work applied to the composite exceeds the strength of the composite and produces apertures in it. The length of the apertures can be varied by controlling the overlap of the upper knuckles and lower knuckles or the size of the knuckles of the rolls. Though the flexibility of the composite is increased by the apertures, the overall strength of the product may be decreased, therefore the preferred product of the present invention employs controlled portions of both apertures and partially fractured or sheared regions.

BRIEF DESCRIPTION OF THE DRAWINGS

FIG. 3 is a perspective view of one embodiment of the present invention;

FIG. 4 is a perspective view of one embodiment of the present invention with a portion broken away for clarity;

FIG. 5 is a perspective view of a further embodiment of the present invention with a portion broken away for clarity.

DETAILED DESCRIPTION OF THE PRESENT INVENTION

Figure 1:
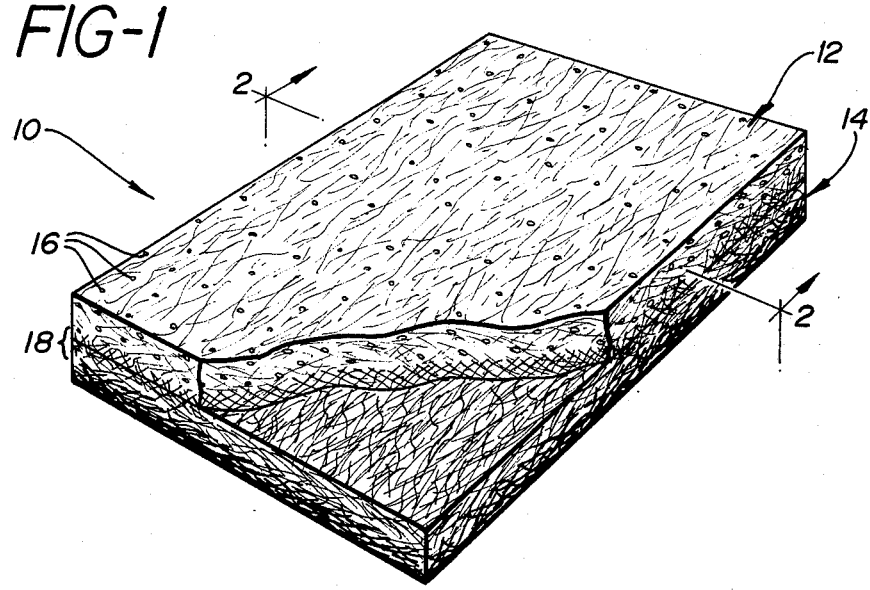
FIG. 1 is a perspective view illustrating one type of starting material for the present invention.

Referring now to the drawings, FIG. 1 represents a perspective view of starting material utilized to make the composite product of the present invention. The starting material 10 is a fibrous web 12 containing at least 200 percent superabsorbent 16 by weight of the web. The superabsorbent particles 16 are distributed substantially throughout the web 12. A wicking layer 14 is provided and the potential transition zone 18 is at the junction of the fibrous web 12 and the wicking layer 14.

Figure 2:
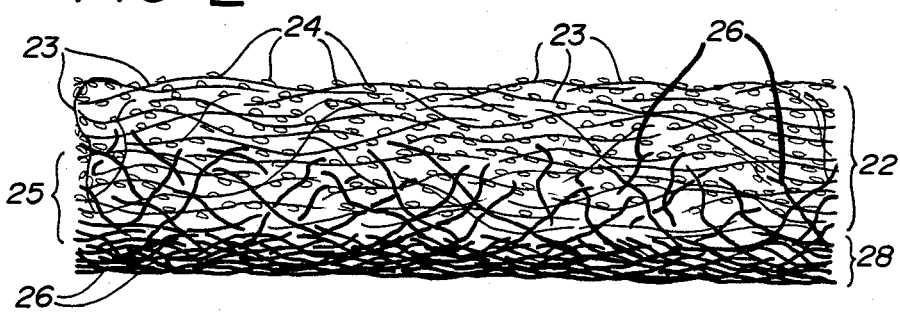
FIG. 2 is an enlarged cross-sectional view of FIG. 1 taken along line 2—2.
Figure 2A:
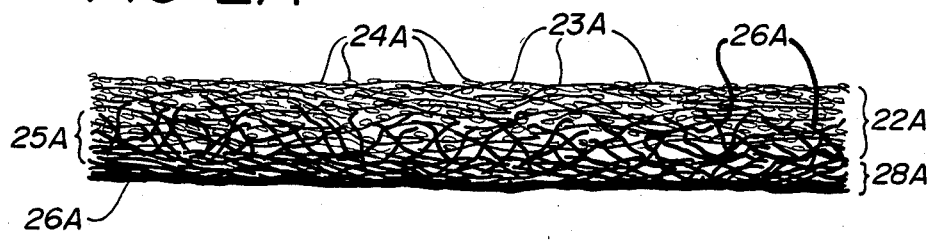
FIG. 2A is a cross-sectional view as in FIG. 2 after compression of the product.

FIG. 2 denotes a section of the product of FIG. 1 which has a fibrous web as an absorbing layer 22. Interspersed among the absorbing layer fibers 23 is superabsorbent material 24. Immediately associated with the absorbing layer is the wicking layer 28. Some portions of the wicking layer fibers 26 extend into and become integral with the absorbing layer 22, thus forming a transition zone 25. By "integral with" is meant in intimate contact with but not requiring physical or chemical bonding. The structure depicted in FIG. 2A is a compressed version of FIG. 2. Upon compression, some of the portions in the wicking layer 28 will extend into and become integral with the fibers of the absorbing layer 22. These wicking layer portions will also be in contact with the superabsorbent material 24. Generally, at least 10 percent moisture is present when the structure is compressed under a pressure sufficient to compact the structure and cause the softened surface of the superabsorbent material to provide the necessary adhesion to the fibers of the absorbing layer so that the composite remains in a compacted state even when dry.

FIG. 3 is a perspective view of an absorbent composite which has been perf-embossed in accordance with the present invention. The composite 30 contains a wicking layer 34 and an absorbing layer 32. Following the perf-embossing, apertures 36 are placed in the composite providing a pattern as shown. The Taber stiffness of the product is at least 75 percent less than that of the product prior to perf-embossing.

FIG. 4 depicts a disposable diaper 40 utilizing an absorbent composite of the present invention. A portion of the drawing is broken away for clarification. The disposable diaper 40 has a liquid-permeable facing 42 and a liquid-impermeable backing 41. In between the facing 42 and the backing 41 is an absorbent composite 43. The composite has wicking layers 44 and 46 and an absorbing layer 45. As is readily seen, the absorbent composite has been perf-embossed. The absorbent composite 43 is held in place between the facing 42 and the backing 41 by glue lines 47. Tape tabs 48 are provided to secure the diaper product 40 about the waist of the wearer.

FIG. 5 is a perspective view of a sanitary napkin 50. The napkin is comprised of a liquid-impermeable shell 52 which contains an absorbent structure 56 and is covered over the upper surface with a liquid-permeable facing 54. The absorbent structure 56 is made in accordance with the present invention and is similar to that of FIG. 3.

These and other products such as incontinent pads, wound dressings, and the like, may be made from the absorbent structures depicted in the drawings.

The fibrous web which contains the superabsorbent and forms the basic absorbing layer for the absorbent composite of the present invention is of substantially high loft and upon dry compression followed by a release has a tendency to return substantially to its original thickness. For instance, fibrous webs formed from synthetic staple fibers, such as polyethylene, polypropylene, polyester, nylon, bicomponent fibers, and the like, are particularly desirable. Melt blown fibrous webs also are suitable. Furthermore, cellulosic fibers such as rayon may be used. Generally, the fibers are air-laid or melt blown to form a web which if needed is then stabilized. Stabilization may be achieved by heat-through bonding, adhesive bonding, point embossing with heat or adhesive, and the like. The stabilizing process is selected according to the fibers used and the process used to form the web. Suitable procedures for forming a web include carding, wet-laying, air-laying, or combinations of these, melt blowing and other suitable known techniques. The fibrous web preferably has a dry bulk recovery of at least about 30 percent, an initial dry bulk of at least 20 cc/gm and a wet bulk of at least 30 cc/gm. The fibrous web generally has a weight less than 4 oz/sq. yd., preferably less than 3 oz/sq. yd.

A wicking layer, generally of wood pulp fibers, is placed on at least one side of the superabsorbent containing fibrous web and in the presence of about 10 percent moisture or more, the product is compressed. The resulting compressed composite generally possesses a Taber stiffness in the machine direction of at least about 130 and sometimes as high as 350.

The superabsorbent material present in an intermittently dispersed form in the absorbing layer is generally a water-insoluble but water-swellable polymeric substance capable of absorbing water in an amount which is at least 10 times the weight of the substance in its dry form. The superabsorbent material is in the form of particles which may be in the shape of fibers, spheres, bits of film, globules, or the like, or may be applied in the form of a liquid monomer solution which is subsequently polymerized. Generally, the polymerized monomer solution provides globules and bits of film-like particles in the structure.

In one type of superabsorbent material, the particles or fibers may be described chemically as having a backbone of natural or synthetic polymers with hydrophilic groups or polymers containing hydrophilic groups being chemically bonded to the backbone or an intimate admixture therewith. Included in this class of materials are such modified natural and regenerated polymers as polysaccharides including, for example, cellulose and starch and regenerated cellulose which are modified by being carboxyalkylated, phosphonoalkylated, sulphoalkylated or phosphorylated to render them highly hydrophilic. Such modified polymers may also be cross-linked to improve their water-insolubility.

These same polysaccharides may also serve, for example, as the backbone onto which other polymer moieties may be bonded by graft copolymerization techniques. Such grafted polysaccharides and their method of manufacture are described in U.S. Pat. No. 4,105,033 to Chatterjee et al. and may be described as polysaccharide chains having grafted thereon a hydrophilic chain of the general formula

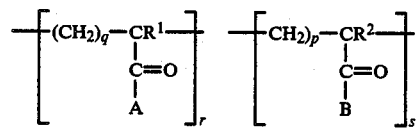

wherein A and B are selected from the group consisting of $-OR^3, -O$ (alkali metal), $-OHNH_3, -NH_2$, wherein $R^1$, $R^2$ and $R_3$ are selected from the group consisting of hydrogen and alkyl having 1 to 4 or more carbon atoms, wherein r is an integer having a value of 0 to about 5000 or more, s is an integer having a value of 0 to about 5000 or more, r plus s is at least 500, p is an integer having a value of zero or 1 and q is an integer having a value of 1 to 4. The preferred hydrophilic chains are hydrolyzed polyacrylonitrile chains and copolymers of polyacrylamide and polysodium acrylate.

In addition to modified natural and regenerated polymers, the hydrocolloid particle component may comprise wholly synthetic hydrophilic particles. Examples of those now known in the art are polyacrylonitrile fibers which may be modified by grafting moieties thereon such as polyvinyl alcohol chains, polyvinyl alcohol itself, hydrophilic polyurethane, poly(alkyl phosphonates), partially hydrolyzed polyacrylamides (e.g., poly(N-N-dimethyl acrylamide), sulfonated polystyrene, or a class of poly(alkylene oxide). These highly hydrophilic synthetic polymers may be modified by other chemical treatments such as cross-linking or hydrolysis. Further examples known in the art are the non-ionic hydrophilic polymers such as polyoxyethylene, polyoxypropylene and mixtures thereof which have been suitably cross-linked, either chemically or by irradiation. Still another more recent type is a derivative of isobutylene-maleic anhydride copolymer.

Hydrophilic polymers formed from water-soluble acrylate monomers, such as sodium, potassium, ammonium (or combination of cations), acrylate, may be placed on the absorbing layer by spraying or otherwise placing a solution thereon followed by polymerization and cross-linking, for example, by irradiation.

In addition, naturally occurring materials such as gums, may be used. For instance, guar gum is suitable.

The superabsorbent material is combined with the fibrous web by any means suitable to distribute the superabsorbent material therein trying to minimize interference by one superabsorbent entity with another upon the swelling of the first. If the superabsorbent material is a powder it may be sprinkled onto the fibrous web either in dry form or the web may be moistened. If the superabsorbent is in granular form it may be desirable to slightly moisten the superabsorbent before placing it in contact with the web. The superabsorbent material will contain particles which range in size from about 0.005 mm in diameter to globules that are continuous along fibers for a distance up to several inches.

Another method of placing the superabsorbent in the web is spraying a monomer solution on the web or saturating the web with a monomer solution followed by polymerization of the monomer. One typical way to polymerize the monomer is by use of irradiation. It is desirable to place the superabsorbent somewhat evenly throughout the fibrous web. However, even if the superabsorbent is powderlike and in the form of a layer, it tends to function better than such a layer has in previously known products. It may be desirable to place more superabsorbent in one area than in another and/or to place the superabsorbent in the structure in predetermined patterns.

Any superabsorbent which absorbs large amounts of liquids is suitable for use in the absorbing layer of the present invention.

As mentioned heretofore, the compressed composite containing the superabsorbent tends to be stiff and substantially non-flexible. Since the end uses of the fibrous web require that the web be soft, flexible and pliable, it has been discovered that perf embossing of the composite provides the necessary reduction in stiffness without damaging the properties of the composite, which are desirable for its end use. Frequently, the Taber stiffness of the composite, wherein the absorbent layer contains at least 200 percent superabsorbent, exceeds 300 Taber stiffness in the machine direction. In the cross-direction the Taber stiffness generally exceeds 70. In order to have a product satisfactory for use in disposable products such as diapers and sanitary napkins, it is necessary to reduce the Taber stiffness value to about 30 or less. The Taber stiffness value is obtained in accordance with the procedure found at ASTM D 2969 and is expressed in gm/lineal cm.

The wicking layer is comprised of hydrophilic fibers, such as rayon fibers, cellulosic fibers, peat moss, acrylic fibers, or mixtures thereof. The cellulosic fibers include wood pulp fibers, cotton linters, and the like. The wood pulp fibers generally are those that are used to form the fluff or fibrous batt layer in conventional absorbent products such as disposable diapers, sanitary napkins, etc. Other cellulosic fibers that might be used are rayon fibers, flax, hemp, jute, ramie, cotton and the like. The fibers or peat moss or mixtures thereof are placed in such a way as to form a layer in which the particles are close to one another so as to provide a higher capillary pressure to promote wicking of liquid in the plane of the layer.

What appears to be only a small difference in capillary pressure is all that is required for one layer to attract and drain liquid from an adjacent layer. The force causing a liquid to enter a cylindrical capillary is expressed by the equation:

$$P = (2\nu \cos \theta)/r$$

wherein the force is represented by the capillary pressure and
P is the capillary pressure,
$\nu$ is the surface tension of the liquid,
$\theta$ is the liquid-fiber contact angle, and
r is the capillary radius.

With a given liquid, the pressure (capillary force) increases with the cosine of the liquid-fiber contact angle (reaching a maximum where the angle is zero) and also increases with narrower capillary radii so that narrower capillaries will draw liquid from wider ones.

The relative wickability between a first fibrous layer and a second layer is affected by both the relative densities of the layers and the relative wettability of the individual fibers in each layer. The individual fibers of the second layer preferably have substantially smaller liquid fiber contact angles than those of the first fibrous layer overcoming the density difference and providing a significant overall increase in capillary pressure to absorb liquid into the second layer.

The fibers of the second layer of fibers (or particles) and/or the density of the layer are selected to create a significant difference in capillary pressure from the first fibrous layer.

The second fibrous (or particle) layer is generally comprised of fibers having a lower liquid-contact angle or wherein the layer is provided with a narrower capillary radii. Examples of such fibers include hydrophilic fibers such as rayon fibers, cellulosic fibers, or peat moss, or mixtures thereof, or acrylic fibers, or the like. Cellulosic fibers include wood pulp fibers, cotton linters and the like.

The wood pulp fibers generally are those that are used to form the fluff or fibrous batt layer in conventional absorbent products such as disposable diapers, sanitary napkins, etc. Other cellulosic fibers that might be used are rayon fibers, flax, hemp, jute, ramie, cotton, and the like. The fiber, or peat moss, or mixtures thereof are placed in such a way as to form a layer in which the particles are close to one another so as to promote wicking of liquid in the plane of the layer.

The wicking layer can be preformed and placed next to the absorbing layer before compression or the wicking layer particles can be air-laid, mechanically entangled therewith, or wet-laid on to the absorbing layer before compression.

The transition zone is a region formed at the junction of the absorbing layer and the wicking layer. Some of the particles, e.g., fibers, of the wicking layer extend into and become integral with the absorbing layer. The region in which the majority of the extending particles lie is identified as the transition zone. In the transition zone, there is a composite of absorbing layer fibers, superabsorbent material, and wicking layer particles. The wicking layer particles which have extended into the absorbing layer are in intimate contact with some of the superabsorbent material of the absorbing layer. This permits the liquid to commence its migration in the z direction to reach the superabsorbent material. As the liquid progresses in the z direction, the superabsorbent material becomes soft and releases the absorbing layer fibers which permit the absorbing layer or return substantially to its uncompressed thickness or more. As the absorbing layer returns to its uncompressed thickness, larger void areas are provided for storage of the liquid and for increased swelling of the superabsorbent material as it absorbs the liquid residing in the void areas. The absorbing layer tends to return to its uncompressed thickness or more, probably because of both the resiliency of the fibers and the swelling of the superabsorbent material.

In order for the absorbing layer fibrous web to provide the necessary medium for absorbing liquid, it is preferred that the fibrous web has an initial dry bulk of at least about 20 cc/gm, a dry bulk recovery of at least 30 percent, (preferably 50 percent), a wet bulk of at least about 30 cc/gm, and a weight of less than about 4 oz/yd$^2$. The initial dry bulk is the area times thickness of the layer under a load of 0.01 pounds per square inch calculated in cubic centimeters. This value is divided by the weight in grams in order to provide the measurement in cubic centimeters per gram. The dry bulk recovery is obtained by subjecting the web to a load of 1.75 psi for five minutes, removing the load and allowing the web to rest for one minute, subjecting the web to a load of 0.01 psi for one minute and then measuring the final dry bulk while under the 0.01 psi load. The dry bulk recovery is the final bulk divided by the initial bulk expressed in percent. The wet bulk is measured in the same manner as the initial dry bulk except that the web has been saturated with water. It has been found that if the fibrous web is provided with a dry bulk recovery of at least 20 percent (preferably 50%), an initial dry bulk of at least 40 cc/gm, a wet bulk of at least 30 cc/gm, with a web weight of less than 4 oz/yd$^2$, the fibrous web can retain superabsorbent material up to at least 1,500 percent of the dry basis weight of the web. It is preferable that the web contain 200 percent to 1,500 percent by weight, dry basis, superabsorbent to the dry basis weight of the web and most preferred is a range from about 400 percent to about 1,200 percent.

It has been discovered that perf-embossing the absorbent composite defined in the present invention results in a flexible, pliable, soft product, which retains substantially its original machine direction strength while having been mechanically worked in such a way as to improve the absorption and reduce the Taber stiffness by at least 75 percent. If the compressed composite used in the present invention is simply put through rolls so as to crush the structure, the product actually becomes stiffer and has a higher Taber stiffness value. It is indeed surprising that the perf-embossing which involves crushing and shearing to some degree, provides the desired product with a substantial reduction in Taber stiffness.

The compressed composite in its substantially stiff form is reduced in moisture content to about 10 percent or less and is then perf-embossed.

In addition to the tenderizing, softening, and improved flexibility of the product, it has been noted that the product absorbs liquid in larger quantities than prior to the perf-embossing treatment. Furthermore, the quick absorption of liquid by the product is not substantially decreased. These qualities are particularly beneficial for a compressed composite product used in a disposable diaper.

An example of a method of preparing the compressed composite of the present invention is as follows. This example is not intended to be limiting in any way and extensions and modifications thereof without departure from the spirit and scope of the invention will become apparent from this example.

EXAMPLE

An absorbing layer for a compressed composite is formed of 67 percent polyester fibers and 33 percent bicomponent fibers. The bicomponent fibers have a polyethylene sheath and a polyester core. The web is heat bonded by passing air at a temperature of 350° F. through the web for about one second or less. The resulting web has a weight of 1.2 oz/sq. yd. The web is coated by flooding it with an aqueous solution of sodium acrylate and acrylic acid. The solution contains 38 percent solids. Excess solution is removed from the web and the web is then subjected to electron beam radiation. This electron beam radiation polymerizes the sodium acrylate to polysodium acrylate. The web is repeatedly flooded with liquid, the excess liquid removed, and each time subjected to irradiation until the amount of dry solids add-on of the polysodium acrylate is 10 times the weight of the web.

The polysodium acrylate coated web is passed beneath a Hammermil that deposits wood pulp fibers onto the polyester web. Vacuum is applied under the polyester web so as to lightly compact the wood pulp fibers onto the web. The wood pulp fibers are present in an amount of about 4 oz/sq. yd. and a layer of the wood pulp fibers is deposited on each side of the polyester web. The surface of the pulp layer is sprayed with water so that the total moisture content of the pulp is about 10 percent by weight. The total structure is then compressed at a level of 640 psi for 30 seconds. Upon release of the pressure, the pulp has formed into a high density layer with a capillary size suitable for liquid wicking and the resilient fiber layer remains compressed. The product containing about 20 percent moisture has a Taber stiffness in the machine direction of about 343, and in the cross-direction 75. If the compressed composite is subjected to perf-embossing at 20 percent moisture, the Taber stiffness in the machine direction increases to about 376 while there is a slight reduction in cross-direction Taber stiffness to a value of about 65. In all instances, the Taber stiffness values are presented in grams per lineal centimeter of the sample.

The compressed composite containing about 20 percent moisture is dried to a moisture content of about 3 percent and subjected to perf-embossing. The perf-embossing rolls are set at 0.05 inch engagement with 40 psi. When the material is processed at the reduced moisture content in this manner, the Taber stiffness in the machine direction is reduced to 30.5 and in the cross-direction to 8.0. It can be clearly seen that the stiffness in the product is reduced by at least 75 percent in each direction.

The perf-embossed product exhibits an improved absorbency in that it shows a 7 percent increase in absorbency after being perf-embossed.

Figure 6:
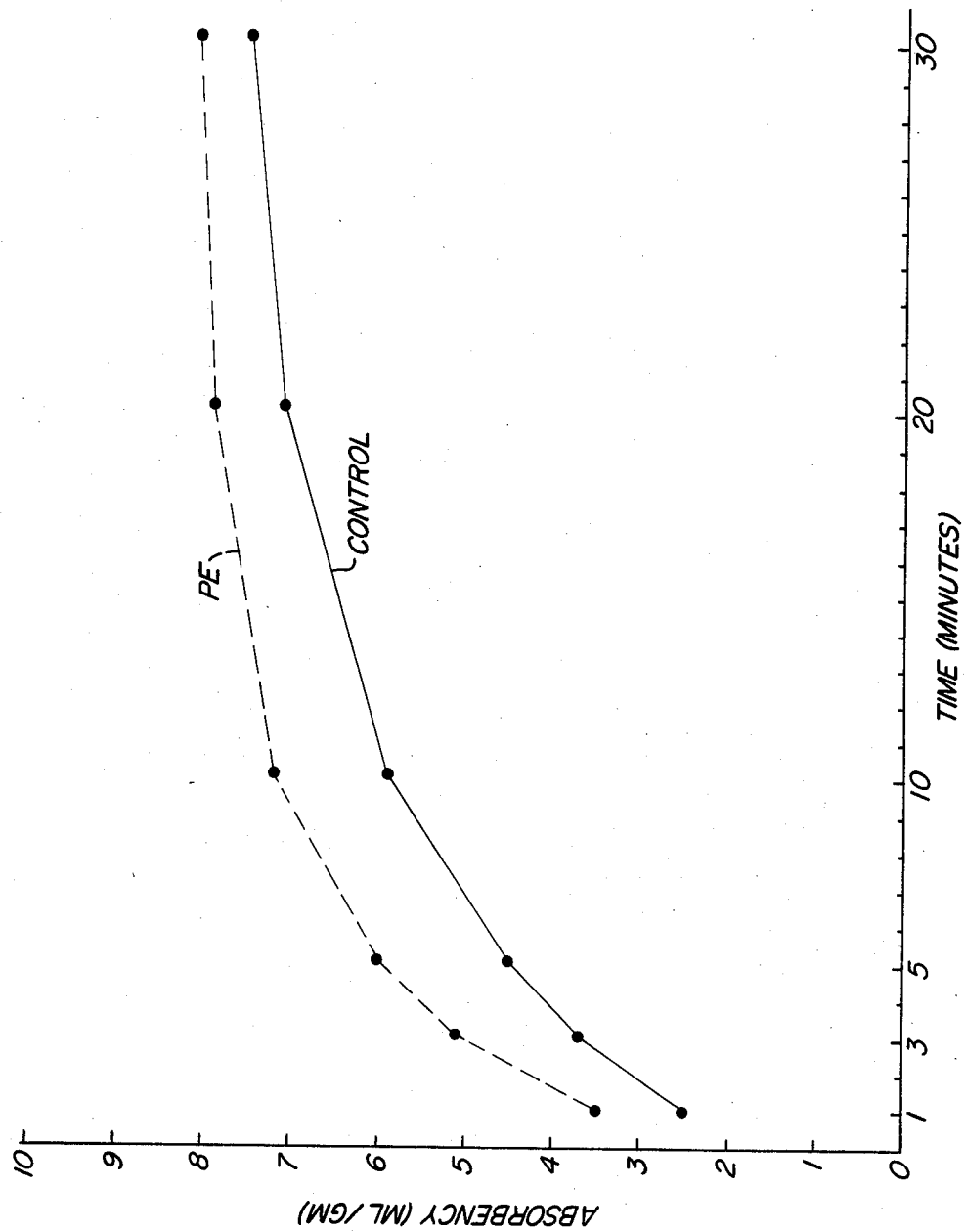
FIG. 6 is a graph depicting the results of the example.

In FIG. 6, it is noted that the perf-embossed (PE) sample absorbs liquid more quickly than the control sample which had not been perf-embossed. In this test of absorbency a GAT device (described in U.S. Pat. No. 4,357,827 is used at 0.5 psi to determine the absorbency of the samples in given time periods. A simulated urine solution (1% NaCl) is used to determine the efficiency of the absorbent structure. In products, such as disposable diapers, the quick acceptance and absorbency of the liquid is needed.

From the foregoing, it will be observed that numerous variations and modifications may be effected without departing from the true spirit and scope of the novel concept of this invention.

I claim:

1. A perf-embossed absorbent composite structure comprising an absorbing layer comprised of a fibrous web having an initial dry bulk of at least about 20 cc/gm, a dry bulk recovery of at least about 30%, a wet bulk of at least about 30 cc/gm and a weight less than about 4 oz/yd and containing at least about 200% superabsorbent, and a wicking layer, said structure having a Taber stiffness value less than about 30.

2. The structure of claim 1 wherein the superabsorbent is present in an amount from about 200% to about 1500%.

3. The structure of claim 2 wherein said superabsorbent is present in an amount from about 400% to about 1200%.

4. The structure of claim 1 wherein said fibrous web is a polyester nonwoven web.

5. The structure of claim 1 wherein said wicking layer is comprised of wood pulp fibers.

6. A disposable diaper having an absorbent core comprised of a perf-embossed composite structure comprising an absorbing layer comprised of a fibrous web having an initial dry bulk of at least about 20 cc/gm, a dry bulk recovery of at least about 30%, a wet bulk of at least about 30 cc/gm and a weight less than about 4 oz/yd and containing at least about 200% superabsorbent, and a wicking layer, said structure having a Taber stiffness value less than about 30.

7. A sanitary napkin having an absorbent core comprised of a perf-embossed absorbent composite structure comprising an absorbing layer comprised of a fibrous web having an initial dry bulk of at least about 20 cc/gm, a dry bulk recovery of at least about 30%, a wet bulk of at least about 30 cc/gm and a weight less than about 4 oz/yd and containing at least about 200% superabsorbent, and a wicking layer, said structure having a Taber stiffness value less than about 30.

8. A method for preparing a flexible, soft absorbent composite structure which comprises:
 (a) drying an absorbent composite structure to a moisture content less tnan about 10% and
 (b) subjecting the dried structure to perf-embossing to reduce the Taber stiffness by at least 75%.

9. The method of claim 8 wherein the Taber stiffness value is reduced to about 30 or less.

* * * * *

UNITED STATES PATENT AND TRADEMARK OFFICE
CERTIFICATE OF CORRECTION

PATENT NO. : 4,596,567

DATED : June 24, 1986

INVENTOR(S) : Michael J. Iskra

It is certified that error appears in the above-identified patent and that said Letters Patent is hereby corrected as shown below:

ON THE TITLE PAGE INSERT:

-- The term of this patent subsequent to December 17, 2002 has been disclaimed. --.

Signed and Sealed this

First Day of December, 1987

Attest:

DONALD J. QUIGG

Attesting Officer

Commissioner of Patents and Trademarks